(12) United States Patent
Yang et al.

(10) Patent No.: US 8,877,991 B2
(45) Date of Patent: Nov. 4, 2014

(54) METHODS FOR THE DEHYDROCHLORINATION OF 1,1,1,3-TETRACHLOROPROPANE TO 1,1,3-TRICHLOROPROPENE

(71) Applicant: Honeywell International, Inc., Morristown, NJ (US)

(72) Inventors: Terris Yang, East Amherst, NY (US); Hsueh Sung Tung, Getzville, NY (US); Robert Johnson, Lancaster, NY (US); Joshua Close, Blasdell, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/181,755

(22) Filed: Feb. 17, 2014

(65) Prior Publication Data

US 2014/0235907 A1 Aug. 21, 2014

Related U.S. Application Data

(60) Provisional application No. 61/766,380, filed on Feb. 19, 2013, provisional application No. 61/766,423, filed on Feb. 19, 2013.

(51) Int. Cl.
*C07C 17/25* (2006.01)
(52) U.S. Cl.
CPC .................................... *C07C 17/25* (2013.01)
USPC ........................................................ 570/228
(58) Field of Classification Search
CPC ............................................................. C07C 17/25
USPC ........................................................ 570/228
See application file for complete search history.

(56) References Cited

U.S. PATENT DOCUMENTS

| 4,535,194 | A | 8/1985 | Woodard |
| 6,534,688 | B2 | 3/2003 | Klausmeyer |
| 8,115,038 | B2 | 2/2012 | Wilson et al. |
| 2009/0030249 | A1 | 1/2009 | Merkel et al. |
| 2012/0035402 | A1 | 2/2012 | Wilson et al. |
| 2012/0142980 | A1 | 6/2012 | Nappa et al. |
| 2012/0142981 | A1 | 6/2012 | Souda et al. |
| 2013/0012743 | A1 | 1/2013 | Wilson et al. |

FOREIGN PATENT DOCUMENTS

| GB | 787936 | 12/1957 |
| WO | 2013022806 A1 | 2/2013 |

OTHER PUBLICATIONS

PCT ISR & Written Opinion issued in PCT/US2014/016855 dated Jul. 7, 2014.

*Primary Examiner* — Elvis O Price
(74) *Attorney, Agent, or Firm* — Bruce O. Bradford

(57) ABSTRACT

This invention relates to a method to improve 1,1,3-trichloropropene selectivity in HCC-250fb (1,1,1,3-tetrachloropropane) dehydrochlorination. In normal practice, $FeCl_3$ is used as the catalyst for the dehydrochlorination of HCC-250fb to produce 1,1,3-trichloropropene. In this invention as source of water is added into the reaction system to inhibit the formation of high boiling compounds such as pentachlorocyclohexene and/or hexachlorocyclohexane. Once source of water is $H_2O$ itself. Another source of water is one or more hydrated metal halides.

20 Claims, No Drawings

METHODS FOR THE DEHYDROCHLORINATION OF 1,1,1,3-TETRACHLOROPROPANE TO 1,1,3-TRICHLOROPROPENE

CROSS-REFERENCE TO RELATED APPLICATIONS

This application claims benefit of U.S. Provisional Patent Application Ser. No. 61/766,380 filed Feb. 19, 2013, the disclosure of which is hereby incorporated herein by reference.

This application also claims benefit of U.S. Provisional Patent Application Ser. No. 61/766,423 filed Feb. 19, 2013, the disclosure of which is hereby incorporated herein by reference.

BACKGROUND OF THE INVENTION

The compound 1,1,3-trichloropropene is useful as a chemical intermediate in the formation of other commercially important compounds. See, for example, U.S. Patent Pub. No. 2012-0142980, the disclosure of which is hereby incorporated herein by reference.

SUMMARY OF THE INVENTION

This invention relates to a method to improve 1,1,3-trichloropropene selectivity in HCC-250fb (1,1,1,3-tetrachloropropane) dehydrochlorination. In normal practice, $FeCl_3$ is used as the catalyst for the dehydrochlorination of HCC-250fb to produce 1,1,3-trichloropropene. See U.S. Patent Pub. No. 2012-0035402 A1, the disclosure of which is hereby incorporated herein by reference.

It has been discovered that when using only $FeCl_3$ as the catalyst for the dehydrochlorination of HCC-250fb, the reaction products contain significant amount of high boiling compounds, ("HBCs") such as pentachlorocyclohexene and/or hexachlorocyclohexane species, in addition to the desired product, namely 1,1,3-trichloropropene. While not wishing to be bound by theory, it is believed that the formation of HBCs is due to the dimerization of 1,1,3-trichloropropene.

Surprisingly, when a source of water was added into the dehydrochlorination reaction HCC-250fb using $FeCl_3$ as dehydrochlorination catalyst, it was found that the selectivity to 1,1,3-trichloropropene was significantly improved. Further study showed that, although $H_2O$ itself cannot perform as an effective catalyst to dehydrochlorinate HCC-250fb to 1,1,3-trichloro-propene, the combination of $FeCl_3$ and $H_2O$ had a positive impact on the reduction of the formation of HBCs. The selectivity to HBCs was reduced to zero when a source of sufficient $H_2O$ was added into the system. These results proved that a source of $H_2O$ can be used as an inhibitor to control the formation of HBCs in the dehydrochlorination of HCC-250fb with $FeCl_3$ as the catalyst.

Thus, one embodiment of the present invention is directed to a process for the dehydrochlorination of HCC-250fb to produce 1,1,3-trichloropropene using $FeCl_3$ as the catalyst, wherein a source of $H_2O$ is added into the system to inhibit the formation of HBCs and to improve 1,1,3-trichloropropene selectivity.

In certain embodiments, the process of the present invention includes a feature wherein the weight ratio of $H_2O$ to HCC-250fb added into the system ranges from above 0% by weight to about 5% by weight, and preferably wherein the weight ratio of $H_2O$ to HCC-250fb is from about 0.01% to 1%.

In addition to the use of water with the $FeCl_3$ catalyst to inhibit the formation of HBCs and to improve 1,1,3-trichloropropene selectivity, it has been found that certain hydrated metal halides can serve as a source of water, and can thus be employed as a co-catalyst for $FeCl_3$, to inhibit the formation of HBCs and to improve 1,1,3-trichloro-propene selectivity. While not wishing to be bound by theory, it is believed that the water from the hydrated metal halides acts much in the same way as the direct addition of water to the reaction, as described above, i.e., successfully inhibiting the formation of HBCs and improving 1,1,3-trichloropropene selectivity.

Thus, another embodiment of the present invention is directed to a process for the dehydrochlorination of HCC-250fb to produce 1,1,3-trichloropropene using a catalyst mixture containing $FeCl_3$ and a source of water comprising one or more hydrated metal halides as a co-catalyst.

In certain embodiments, the hydrated metal halide co-catalyst comprises $BaCl_2.2H_2O$. Applicant believes that any hydrated metal halide will be useful herein, such as $CrCl_3.6H_2O$, $CuCl_2.2H_2O$, $FeCl_2.4H_2O$, $FeCl_3.6H_2O$, $MnCl_2.6H_2O$, $NiCl_2.6H_2O$, $SnCl_2.2H_2O$, $CoBr_2.6H_2O$, $VI_3.6H_2O$ or a mixture thereof, can be used as a co-catalyst source of water for the dehydrochlorination of HCC-250fb using $FeCl_3$ as the catalyst.

In certain embodiments, the weight ratio of $FeCl_3$ to HCC-250fb is from above 0 ppm to 10,000 ppm and the weight ratio of $BaCl_2.2H_2O$ to HCC-250fb is from above 0% to 10%.

In certain embodiments, the weight ratio of $FeCl_3$ to HCC-250fb is from 100 ppm to 2000 ppm and the weight ratio of $BaCl_2.2H_2O$ to HCC-250fb is from 0.1% to 5%.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As described above, it has been discovered that the addition of a source of water selected from $H_2O$ and/or one or more hydrated metal halide co-catalysts to the HCC-250fb dehydrochlorination process using $FeCl_3$ as the main catalyst can inhibit the formation of unwanted HBCs and improve the selectivity to 1,1,3-trichloropropene significantly, which can be beneficial to the reduction of process waste and simplify the future separation of crude product, and therefore reduce the production cost.

The dehydrochlorination reactions are preferably carried out under conditions to attain a HCC-250fb conversion of about 20 mol % or higher, preferably about 40 mol % or higher, and even more preferably about 50 mol % or higher, and a desired 1,1,3-trichloro-propene product selectivity of at least about 50 mol % or higher, preferably at least about 70 mol % or higher, and more preferably at least about 95 mol % or higher. Selectivity is calculated by number of moles of product formed divided by number of moles of reactant consumed.

Useful reaction temperatures for the dehydrochlorination reactions may range from about 50° C. to about 300° C. Preferred temperatures may range from about 70° C. to about 150° C., and more preferred temperatures may range from about 100° C. to about 125° C. One especially preferred reaction temperature is about 120° C. The reaction may be conducted at atmospheric pressure, super-atmospheric pressure or under vacuum. The vacuum pressure can be from about 0 torr to about 760 torr. Contact time of the reactant starting materials with the catalyst mixture may range from about 1 to 10 hours, preferably from about 2 to 8 hours, more preferably about 4 hours, however, longer or shorter times can be used.

The following Table shows the result of testing done in accordance with one embodiment of the present invention.

HCC-250fb Dehydrochlorination

| Reaction Temp, ° C. | Reaction Time, hr | FeCl3/250fb, ppmw | H2O/25fb, ppmw | 250fb conv.,% mol | 1,1,3 Sel., % mol | HCH Sel., % mol |
|---|---|---|---|---|---|---|
| 120 | 4 | 752 | 0 | 96.76% | 91.42% | 8.57% |
| 120 | 4 | 756 | 1087 | 88.92% | 96.10% | 3.58% |
| 120 | 4 | 745 | 2089 | 85.84% | 97.11% | 2.86% |
| 120 | 4 | 743 | 2979 | 56.78% | 99.46% | 0.51% |
| 120 | 4 | 796 | 3574 | 33.58% | 100.00% | 0.00% |

In another embodiment, the hydrated metal halide $BaCl_2 \cdot 2H_2O$ was tested as the dehydrochlorination catalyst for HCC-250fb, with only 6.5% mol of 250fb conversion achieved under reaction conditions of 120° C., 8 hours of residence time and 2.3% of $BaCl_2 \cdot 2H_2O/250fb$ weight ratio. While the yield of 1,1,3-trichloropropene was low, there were no HBCs detected in the reaction product.

Further study showed that, the combination of $FeCl_3$ and $BaCl_2 \cdot 2H_2O$ had both a positive impact on the selectivity to 1,1,3-trichloropropene as well as a reduction of the formation of HBCs. The addition of $BaCl_2 \cdot 2H_2O$ to the mixture of HCC-250fb and $FeCl_3$ reduced the selectivity to HBCs and increased the selectivity to 1,1,3-trichloro-propene significantly. These results proved that the mixture of $FeCl_3$ and $BaCl_2 \cdot 2H_2O$ can be used as an effective catalyst to control the formation of HBCs in the dehydrochlorination of HCC-250fb. It is expected that other hydrated metal halide compounds will provide a similar effect.

The mixture of $BaCl_2 \cdot 2H_2O$ and $FeCl_3$ can be used as the catalyst for the dehydrochlorination of HCC-250fb to produce 1,1,3-trichloropropene, which can reduce the selectivity to HBCs and improve the selectivity to 1,1,3-trichloropropene. As HBCs cannot be converted into the desired product, the new catalyst mixture will be beneficial to the reduction of process waste and simplify the future separation of crude product, and therefore reduce the overall production cost.

The following examples provide additional details regarding various embodiments of the present invention.

Example 1

A 500 ml glass flask (reactor) equipped with a magnetic stirring bar and a total condenser was charged with 150.8 g HCC-250fb (Vulcan, 99.9 wt %) and 0.113 g $FeCl_3$. The reactor was stirred and heated to 120±2° C. via an oil bath. After 4 hours, the reactor was removed from the oil bath and cooled down to room temperature. Then the mixture in the reactor was filtered, washed with deionized (D.I.) water and dried with $MgSO_4$. By GC analysis, the reaction mixture contained 81.1 wt % of 1,1,3-trichloropropene, 3.7 wt % of HCC-250fb, and 15.2 wt % of HBCs, representing a HCC-250fb conversion of 96.8 mol %, 1,1,3-trichloropropene selectivity of 91.4 mol %, and HBCs selectivity of 8.6 mol %.

Example 2

100.6 g HCC-250fb (Vulcan, 99.9 wt %) and 0.35 g D.I. $H_2O$ were charged into the reactor with the same reaction conditions and procedure followed as described in Example 1. By GC analysis, the reaction mixture contained 0.5 wt % of 1,1,3-trichloro-propene and 99.5 wt % of HCC-250fb with no HBCs detected, representing a HCC-250fb conversion of 0.6 mol % and 1,1,3-trichloropropene selectivity of 100 mol %.

Example 3

The same apparatus as described in Example 1 was charged with 100.3 g HCC-250fb (Vulcan, 99.9 wt %), 0.076 g $FeCl_3$ and 0.11 g D.I. $H_2O$. The same reaction conditions and procedure were followed as in Example 1. By GC analysis, the reaction mixture contained 80.8 wt % of 1,1,3-trichloropropene, 13.1 wt % of HCC-250fb and 6.1 wt % of HBCs, representing a HCC-250fb conversion of 88.9 mol %, 1,1,3-trichloro-propene selectivity of 96.4 mol %, and HBCs selectivity of 3.6 mol %.

Example 4

100.2 g HCC-250fb (Vulcan, 99.9 wt %), 0.08 g $FeCl_3$ and 0.36 g D.I. $H_2O$ were charged into the reactor with the same reaction conditions and procedure followed as described in Example 1. By GC analysis, the reaction mixture contained 28.8 wt % of 1,1,3-trichloropropene, 71.2 wt % of HCC-250fb with no HBCs detected, representing a HCC-250fb conversion of 33.6 mol % and 1,1,3-trichloropropene selectivity of 100 mol %.

Example 5

100.7 g HCC-250fb (Vulcan, 99.9 wt %), 0.075 g $FeCl_3$ and 0.3 g D.I. $H_2O$ were charged into the reactor with the same reaction conditions and procedure followed as described in Example 1. By GC analysis, the reaction mixture contained 50.8 wt % of 1,1,3-trichloropropene, 48.6 wt % of HCC-250fb and 0.5 wt % of HBCs, representing a HCC-250fb conversion of 56.8 mol %, 1,1,3-trichloropropene selectivity of 99.5 mol % and HBCs selectivity of 0.5 mol %.

Example 6

The same apparatus as described in Example 1 was charged with 150.5 g HCC-250fb (Vulcan, 99.9 wt %) and 3.5 g BaCl$_2$.2H$_2$O. The same reaction conditions and procedure were followed as in Example 1. By GC analysis, the reaction mixture contained 5.2 wt % of 1,1,3-trichloropropene and 94.8 wt % of HCC-250fb with no HBCs detected, representing a HCC-250fb conversion of 6.5 mol % and 1,1,3-trichloropropene selectivity of 100 mol %.

Example 7

150.5 g HCC-250fb (Vulcan, 99.9 wt %), 0.117 g FeCl$_3$ and 0.88 g BaCl$_2$.2H$_2$O were charged into the reactor with the same reaction conditions and procedure followed as described in Example 1. By GC analysis, the reaction mixture contained 77.9 wt % of 1,1,3-trichloropropene, 15.7 wt % of HCC-250fb, and 6.3 wt % of HBCs, representing a HCC-250fb conversion of 86.6 mol %, 1,1,3-trichloropropene selectivity of 96.1 mol %, and HBCs selectivity of 3.9 mol %.

Example 8

150.1 g HCC-250fb (Vulcan, 99.9 wt %), 0.112 g FeCl$_3$ and 3.5 g BaCl$_2$.2H$_2$O were charged into the reactor with the same reaction conditions and procedure followed as described in Example 1. By GC analysis, the reaction mixture contained 38.9 wt % of 1,1,3-trichloropropene, 47.3 wt % of HCC-250fb, and 0.02 wt % of HBCs, representing a HCC-250fb conversion of 50.7 mol %, 1,1,3-trichloropropene selectivity of 99.9 mol %, and HBCs selectivity of 0.03 mol %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the catalytic dehydrochlorination of HCC-250fb to produce 1,1,3-trichloropropene using a catalyst or catalyst mixture comprising iron halides, wherein a source of water is added into the system to inhibit the formation of high boiling compounds including pentachlorocyclohexene and/or hexachlorocyclohexane.

2. The process of claim 1, wherein the source of water comprises H$_2$O.

3. The process of claim 2, wherein the iron halide compounds comprise chloride compounds.

4. The process of claim 3, wherein the iron chloride compound comprises FeCl$_3$.

5. The process of claim 3, wherein the iron chloride compound comprises FeCl$_2$.

6. The process of claim 2, wherein the weight ratio of H$_2$O to HCC-250fb added into the system can be ranged from above 0% by weight to 5% by weight.

7. The process of claim 2, wherein the weight ratio of H$_2$O to HCC-250fb is from about 0.01% to about 1%.

8. The process of claim 1, wherein the source of water comprises one or more hydrated metal halides.

9. The process of claim 8, wherein the hydrated metal halide is selected from the group consisting of BaCl$_2$.2H$_2$O, CrCl$_3$.6H$_2$O, CuCl$_2$.2H$_2$O, FeCl$_2$.4H$_2$O, FeCl$_3$.6H$_2$O, MnCl$_2$.6H$_2$O, NiCl$_2$.6H$_2$O, SnCl$_2$.2H$_2$O, CoBr$_2$.6H$_2$O, VI$_3$.6H$_2$O and mixtures thereof.

10. The process of claim 8, wherein the hydrated metal halide comprises BaCl$_2$.2H$_2$O and the iron halide comprises FeCl$_3$.

11. The process of claim 10, wherein the weight ratio of FeCl$_3$ to HCC-250fb is from above 0 to 10,000 ppm and the weight ratio of BaCl$_2$.2H$_2$O to HCC-250fb is from above 0 to 10%.

12. The process of claim 10, wherein the weight ratio of FeCl$_3$ to HCC-250fb is from 100 to 2000 ppm and the weight ratio of BaCl$_2$.2H$_2$O to HCC-250fb is from 0.1% to 5%.

13. The process of claim 1, wherein the dehydrochlorination reaction is carried out under conditions to attain a starting material HCC-250fb conversion of at least about 20 mol % or higher.

14. The process of claim 1, wherein the dehydrochlorination reaction is carried out under conditions to attain a starting material HCC-250fb conversion of at least about 40 mol % or higher.

15. The process of claim 1, wherein the dehydrochlorination reaction is carried out under conditions to attain a starting material HCC-250fb conversion of at least about 50 mol % or higher.

16. A process for the dehydrochlorination of HCC-250fb to produce 1,1,3-trichloropropene using one or more iron halide compounds as the catalyst, wherein a source of water is added into the system to improve 1,1,3-trichloropropene selectivity.

17. The process of claim 16, wherein the source of water comprises H$_2$O.

18. The process of claim 16, wherein the source of water comprises one or more hydrated metal halides.

19. The process of claim 16, wherein the selectivity to the formation of 1,1,3-trichloropropene is at least about 70 mol % or higher.

20. The process of claim 16, wherein the selectivity to the formation of 1,1,3-trichloropropene is at least about 95 mol % or higher.

* * * * *